US008939435B2

(12) United States Patent  
Gordon et al.

(10) Patent No.: US 8,939,435 B2  
(45) Date of Patent: Jan. 27, 2015

(54) DEVICE FOR DELIVERY OF VOLATILE LIQUIDS TO GASEOUS ENVIRONMENT UTILIZING A GAS GENERATING CELL

(75) Inventors: John Howard Gordon, Salt Lake City, UT (US); Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 281 days.

(21) Appl. No.: 13/487,976

(22) Filed: Jun. 4, 2012

(65) Prior Publication Data

US 2012/0305667 A1  Dec. 6, 2012

Related U.S. Application Data

(60) Provisional application No. 61/493,127, filed on Jun. 3, 2011.

(51) Int. Cl.
*B01F 3/04* (2006.01)
*A61L 9/12* (2006.01)

(52) U.S. Cl.
CPC ............... *A61L 9/12* (2013.01); *A61L 2209/11* (2013.01); *A61L 2209/133* (2013.01); *A61L 2209/135* (2013.01); *Y10S 261/88* (2013.01)
USPC ............ 261/26; 261/34.1; 261/104; 261/107; 261/DIG. 88; 261/124

(58) Field of Classification Search
CPC ..... B01F 3/04; B01F 3/04007; B01F 3/04085
USPC .................... 261/26, 34.1, 104, 107, DIG. 88; 422/124
See application file for complete search history.

(56) References Cited

U.S. PATENT DOCUMENTS

| 446,953 A | 2/1891 | Robert |
| 575,365 A | 1/1897 | Mayer et al. |
| 806,844 A | 12/1905 | Rosenstock |
| 957,449 A | 5/1910 | Walz |
| 976,992 A | 11/1910 | Effantin et al. |
| 1,099,720 A | 6/1914 | Peck |

(Continued)

FOREIGN PATENT DOCUMENTS

| FR | 2082589 | 12/1971 |
| GB | 191400142 | 0/1914 |

(Continued)

OTHER PUBLICATIONS

Hwu, Davis D., "PCT International Search Report for PCT/US05/23523", (Dec. 4, 2006),1-3.

(Continued)

*Primary Examiner* — Robert A Hopkins  
(74) *Attorney, Agent, or Firm* — Jeffrey T. Holman (57) ABSTRACT

A delivery apparatus includes a volatile agent source, a controller, and an emanator material. The volatile agent source stores a volume of a volatile agent such as a fragrance. The volatile agent source includes an outlet for delivery of the volatile agent from the volatile agent source. The controller controls a delivery rate of the volatile agent from the volatile agent source. The emanator material is disposed at approximately the outlet of the volatile agent source. The emanator material absorbs at least a portion of the volatile agent and maintains the volatile agent until the volatile agent evaporates into an ambient environment.

29 Claims, 4 Drawing Sheets (56) References Cited

U.S. PATENT DOCUMENTS

| | | | |
|---|---|---|---|
| 1,222,756 A | 4/1917 | Griner |
| 1,921,821 A | 8/1933 | Higgins |
| 2,219,959 A | 10/1940 | Laidley |
| 2,236,525 A | 4/1941 | Davis et al. |
| 2,481,296 A | 9/1949 | Dupuy |
| 2,670,236 A | 2/1954 | Bradburn |
| 2,710,164 A | 6/1955 | Hare |
| 2,740,662 A | 4/1956 | Scott |
| 2,801,879 A | 8/1957 | Dick |
| 2,867,360 A | 1/1959 | Sharma |
| 2,991,517 A | 7/1961 | Bundy |
| 3,127,786 A | 4/1964 | Wooley |
| 3,169,705 A | 2/1965 | Geiger |
| 3,254,841 A | 6/1966 | Loncker |
| 3,482,929 A | 12/1969 | Gentil |
| 3,685,734 A | 8/1972 | Paciorek et al. |
| 3,804,592 A | 4/1974 | Garbe et al. |
| 3,955,930 A | 5/1976 | Shapiro |
| 4,017,030 A | 4/1977 | Coplan et al. |
| 4,158,440 A | 6/1979 | Sullivan et al. |
| 4,166,478 A | 9/1979 | Sugimura et al. |
| 4,169,757 A | 10/1979 | Kirjavainen |
| 4,265,373 A | 5/1981 | Stoody |
| 4,294,778 A | 10/1981 | Deluca |
| 4,312,347 A | 1/1982 | Magoon et al. |
| 4,328,843 A | 5/1982 | Fujii |
| 4,339,079 A | 7/1982 | Sato et al. |
| 4,399,942 A | 8/1983 | Chand |
| 4,408,635 A | 10/1983 | Packer |
| 4,427,030 A | 1/1984 | Jouwsma |
| 4,468,220 A | 8/1984 | Willbanks |
| 4,477,414 A | 10/1984 | Muramoto et al. |
| 4,522,698 A | 6/1985 | Maget |
| 4,526,320 A | 7/1985 | von Philipp et al. |
| 4,552,561 A | 11/1985 | Eckenhoff et al. |
| 4,621,768 A | 11/1986 | Lhoste et al. |
| 4,632,310 A | 12/1986 | Konicek |
| 4,674,494 A | 6/1987 | Wiencek |
| 4,687,423 A | 8/1987 | Maget et al. |
| 4,697,549 A | 10/1987 | Hair |
| 4,753,389 A | 6/1988 | Davis |
| 4,809,912 A | 3/1989 | Santini |
| 4,846,003 A | 7/1989 | Marquiss |
| 4,871,544 A | 10/1989 | Eckenhoff |
| 4,886,514 A | 12/1989 | Maget |
| 4,917,301 A | 4/1990 | Munteanu |
| 4,948,047 A | 8/1990 | Zembrodt |
| 4,966,767 A | 10/1990 | Eckenhoff |
| 4,969,874 A | 11/1990 | Michel et al. |
| 4,995,555 A | 2/1991 | Woodruff |
| 5,074,252 A | 12/1991 | Morgan, Jr. |
| 5,143,259 A | 9/1992 | Williams |
| 5,161,680 A | 11/1992 | Badgley |
| 5,196,002 A | 3/1993 | Hanover et al. |
| 5,312,389 A | 5/1994 | Theeuwes et al. |
| 5,357,793 A | 10/1994 | Jouwsma |
| 5,368,863 A | 11/1994 | Eckenhoff et al. |
| 5,398,851 A | 3/1995 | Sancoff et al. |
| 5,427,870 A | 6/1995 | Joshi et al. |
| 5,437,410 A | 8/1995 | Babasade |
| 5,454,922 A | 10/1995 | Joshi et al. |
| 5,462,741 A | 10/1995 | Carr et al. |
| 5,474,785 A | 12/1995 | Wright et al. |
| 5,538,605 A | 7/1996 | Joshi et al. |
| 5,549,037 A | 8/1996 | Stumphauzer et al. |
| 5,567,287 A | 10/1996 | Joshi et al. |
| 5,591,395 A | 1/1997 | Schroeder et al. |
| 5,591,409 A * | 1/1997 | Watkins .................. 422/110 |
| 5,593,552 A | 1/1997 | Joshi et al. |
| 5,638,868 A | 6/1997 | Loran |
| 5,647,515 A | 7/1997 | Zwijnenberg et al. |
| 5,681,435 A | 10/1997 | Joshi et al. |
| 5,700,245 A | 12/1997 | Sancoff et al. |
| 5,707,499 A | 1/1998 | Joshi et al. |
| 5,714,160 A | 2/1998 | Magruder et al. |
| 5,744,014 A | 4/1998 | Gordon et al. |
| 5,765,751 A | 6/1998 | Joshi |
| 5,785,688 A | 7/1998 | Joshi et al. |
| 5,810,253 A | 9/1998 | Ohayon |
| 5,855,761 A | 1/1999 | Joshi |
| 5,857,590 A | 1/1999 | Kao et al. |
| 5,871,125 A | 2/1999 | Gross |
| 5,899,381 A | 5/1999 | Gordon et al. |
| 5,915,925 A | 6/1999 | North, Jr. |
| 5,921,251 A | 7/1999 | Joshi |
| 5,932,204 A | 8/1999 | Joshi |
| 5,951,538 A | 9/1999 | Joshi et al. |
| 5,954,268 A | 9/1999 | Joshi et al. |
| 5,971,713 A | 10/1999 | North, Jr. |
| 5,993,854 A | 11/1999 | Needleman et al. |
| 5,997,821 A | 12/1999 | Joshi |
| 6,042,704 A | 3/2000 | Joshi et al. |
| 6,045,055 A | 4/2000 | Joshi et al. |
| 6,060,196 A | 5/2000 | Gordon et al. |
| 6,082,117 A | 7/2000 | Funatsu et al. |
| 6,109,539 A | 8/2000 | Joshi et al. |
| 6,135,126 A | 10/2000 | Joshi |
| 6,220,267 B1 | 4/2001 | Joshi |
| 6,283,461 B1 | 9/2001 | Joshi et al. |
| 6,289,241 B1 | 9/2001 | Phipps |
| 6,378,780 B1 | 4/2002 | Martens, III et al. |
| 6,415,808 B2 | 7/2002 | Joshi |
| 6,419,163 B1 | 7/2002 | Joshi |
| 6,491,684 B1 | 12/2002 | Joshi et al. |
| 6,527,012 B1 | 3/2003 | Weber |
| 6,553,712 B1 | 4/2003 | Majerowski et al. |
| 6,622,755 B2 | 9/2003 | Weber |
| 6,715,300 B2 | 4/2004 | Longsworth |
| 6,729,552 B1 | 5/2004 | McEwen et al. |
| 6,786,474 B2 * | 9/2004 | Watkins et al. ................. 261/26 |
| 6,787,008 B2 | 9/2004 | Joshi et al. |
| 6,805,306 B1 | 10/2004 | Huang |
| 6,813,944 B2 | 11/2004 | Mayer et al. |
| 6,901,965 B2 | 6/2005 | Baltes et al. |
| 6,923,383 B1 | 8/2005 | Joshi |
| 7,048,009 B2 | 5/2006 | Verhaeghe |
| 7,149,417 B2 | 12/2006 | Joshi et al. |
| 7,614,568 B2 | 11/2009 | Joshi et al. |
| 8,061,280 B2 | 11/2011 | Gordon et al. |
| 8,113,390 B2 | 2/2012 | Wold et al. |
| 8,353,426 B2 | 1/2013 | Wold et al. |
| 2002/0158156 A1 | 10/2002 | Joshi et al. |
| 2002/0175191 A1 | 11/2002 | Joshi et al. |
| 2003/0094503 A1 | 5/2003 | Rymer et al. |
| 2004/0135005 A1 | 7/2004 | Duquet |
| 2004/0261790 A1 | 12/2004 | Joshi et al. |
| 2005/0023371 A1 | 2/2005 | Joshi et al. |
| 2005/0035143 A1 | 2/2005 | Massaro et al. |
| 2005/0150449 A1 | 7/2005 | Matsunaga et al. |
| 2005/0175331 A1 | 8/2005 | Tam et al. |
| 2005/0218074 A1 | 10/2005 | Pollock |
| 2005/0279776 A1 | 12/2005 | Decottignies et al. |
| 2006/0039685 A1 | 2/2006 | Berrido et al. |
| 2007/0001024 A1 | 1/2007 | Wold et al. |
| 2007/0025869 A1 | 2/2007 | Gordon |
| 2008/0191370 A1 | 8/2008 | Pankhurst et al. |
| 2008/0257412 A1 | 10/2008 | Gordon |
| 2008/0308647 A1 | 12/2008 | Maget et al. |
| 2009/0173799 A1 | 7/2009 | Litten-Brown et al. |
| 2010/0015009 A1 | 1/2010 | Wallace et al. |
| 2010/0022993 A1 | 1/2010 | Gordon et al. |
| 2010/0222770 A1 | 9/2010 | Gordon et al. |
| 2011/0303760 A1 | 12/2011 | Joshi et al. |
| 2012/0031497 A1 | 2/2012 | Gordon |
| 2012/0031503 A1 | 2/2012 | Gordon |
| 2012/0031513 A1 | 2/2012 | Gordon |
| 2012/0037242 A1 | 2/2012 | Gordon et al. |
| 2012/0037658 A1 | 2/2012 | Gordon et al. |

(56) References Cited

U.S. PATENT DOCUMENTS

| | | | |
|---|---|---|---|
| 2012/0160930 A1 | 6/2012 | Joshi | |
| 2013/0026194 A1 | 1/2013 | Wold et al. | |

FOREIGN PATENT DOCUMENTS

| | | |
|---|---|---|
| JP | 00374/140 | 1/1940 |
| JP | 4221275 | 12/1967 |
| JP | 155896/1978 | 5/1980 |
| JP | 91380/1983 | 9/1983 |
| JP | 62-33102 | 2/1987 |
| JP | 305870/1988 | 12/1988 |
| JP | 181871/1989 | 7/1989 |
| JP | 64648/1991 | 6/1991 |
| JP | 70141/1991 | 7/1991 |
| JP | 00156/1993 | 1/1993 |
| JP | 05-262602 | 10/1993 |
| JP | 317401/1993 | 12/1993 |
| JP | 155367/1995 | 6/1995 |
| JP | 182783/1997 | 7/1997 |
| JP | 09-253185 | 9/1997 |
| JP | 09-276386 | 10/1997 |
| JP | 276387/1997 | 10/1997 |
| JP | 47253/1999 | 2/1999 |
| JP | 0724201 | 8/2008 |
| WO | WO-88/08308 | 11/1988 |
| WO | 00/72951 | 12/2000 |
| WO | WO-00/76645 | 12/2000 |
| WO | WO-2004/020005 | 3/2004 |
| WO | 2006/007559 | 1/2006 |

OTHER PUBLICATIONS

Hwu, Davis D., "PCT Written Opinion of the International Searching Authority for PCT/US05/23523", (Dec. 4, 2006),1-3.
Nguyen, Dinh Q., "PCT International Search Report for PCT/US05/21022", (May 10, 2007),1-3.
Nguyen, Dinh Q., "PCT Written Opinion of the International Searching Authority for PCT/US05/21022", (May 10, 2007),1-3.
Nguyen, Dinh Q., "Office Action Summary for U.S. Appl. No. 10/868,203", (Aug. 14, 2007),1-5.
Kim, Christopher S., "Office Action for U.S. Appl. No. 09/649,563 sent Sep. 10, 2003",1-5.
Kim, Christopher S., "Office Action for U.S. Appl. No. 09/649,563 send Apr. 13, 2004",1-6.
Kim, Christopher S., "Office Action for U.S. Appl. No. 09/649,563 sent Aug. 25, 2006",1-6.
Kim, Christophe S., "Office Action for U.S. Appl. No. 09/649,563 sent Jun. 12, 2007",1-7.
Nguyen, Dinh "Office Action for U.S. Appl. No. 11/160,642 sent May 1, 2008",1-7.
Kim, "Office Action for U.S. Appl. No. 09/649,563 sent Feb. 15, 2008",1-9.
Nguyen, Dinh "Office Action for U.S. Appl. No. 10/868,203 sent Mar. 17, 2008",1-7.
Varga, Viktoria "European Search Report for EP05790118.3 sent Nov. 7, 2007",1-3.
Joshi, et al., "Application for U.S. Appl. No. 09/649,563 filed Aug. 28, 2000",1-33.
Kim, "Office Action for U.S. Appl. No. 09/649,563 sent Jul. 9, 2008",1-8.
Varga, Viktoria "Communication pursuant to Article 94(3) EPC", (Aug. 20, 2008),1-6.
Kim, "Office Action for U.S. Appl. No. 09/649,563 sent Dec. 30, 2008",1-8.
Nguyen, Dinh "Office Action for U.S. Appl. No. 10/868,203 sent Dec. 15, 2008",1-6.
Nguyen, Dinh "Office Action for U.S. Appl. No. 11/160,642 sent Dec. 10, 2008", 1-8.
Kang, Sang Yoon "Written Opinion of the International Searching Authority", International App. No. PCT/US2008/080988, (Jul. 2, 2009),1-4.
Kang, Sang Yoon "International Search Report", International App. No. PCT/US2008/080988, (Jul. 2, 2009),1-3.
Kim, Myeong Hee "International Search Report", International Search Report for PCT/US2010/057421, (Aug. 26, 2011),1-3.
Kim, Myeong Hee "Written Opinion of the International Searching Authority", Written Opinion for PCT/US2010/057421, (Aug. 26, 2011),1-4.
Shelborne, K "Non-Final Office Action", U.S. Appl. No. 08/880,124, (Apr. 13, 1998),1-6.
Shelborne, K "Non-Final Office Action", U.S. Appl. No. 08/880,124, (Oct. 6, 1998),1-3.
Guillem, Gisbert I., "European Search Report", EP app. No. 98930214.6 (corresponding to U.S. Appl. No. 08/880,124), (Dec. 28, 2009),1-3.
Guillem, Gisbert I., "Communication Pursuant to Article 94(3) EPC (European Office Action)", EP App No. 98930214.6 (corresponding to U.S. Appl. No. 08/880,124), (Oct. 15, 2010),1-6.
Kokubo, Katsui "Notice of Reason for Rejection", JP App. No. 11-504624 (Corresponding to U.S. Appl. No. 08/880,124), (Jul. 29, 2008),1-5.
Nakazawa, Noboru "Notice of Reason for Rejection", JP App. No. 11-504624 (Corresponding to U.S. Appl. No. 08/880,124), (May 19, 2009),1-6.
Unknown, "English Translation of Utility Model Publication JP 42-21275", Translation of JP 42-21275 (supplied by Japanese patent office), (Dec. 7, 1967),1-4.
Kawamura, Norio "English Abstract of JP 07-24201", English Abstract of JP 07-24201, (Aug. 21, 2008),1-2.
Lawrence, Dorithia "International Search Report", PCT US 98/12379 (corresponding to U.S. Appl. No. 08/880,124), (Sep. 30, 1998),1.
Shelborne, Kathryne E., "International Preliminary Examination Report", PCT US 98/12379 (corresponding to U.S. Appl. No. 08/880,124), (Feb. 11, 1999),1-4.
Weldon, K "Non-Final Office Action", U.S. Appl. No. 09/028,372, (Jun. 22, 1999),1-7.
Weldon, K "Final Office Action", U.S. Appl. No. 09/028,372, (Nov. 15, 1999),1-7.
Moeremans, Benoit "Communication Pursuant to Article 94(3) EPC", EP App. No. 99925948.4, (Sep. 12, 2011),1-5.
Honma, T "Official Notice of Reason of Preliminary Rejection (Japan)", JP App. No. 621054/2000 (Corresponding to U.S. Appl. No. 09/028,372), (Mar. 23, 2004),1-4.
Honma, T "Official Notice of Reason of Preliminary Rejection", JP App. No. 621054/2000 (Corresponding to U.S. Appl. No. 09/028,372), (Jun. 14, 2005),1-3.
Unknown Japanese Patent Examiner, "Official Notice of Reason for Final Rejection", JP App. No. 621054/2000 (Corresponding to U.S. Appl. No. 09/028,372), (May 30, 2006),1.
Inoue, Perfume "English Abstract", JP App. No. 64648/1991, (Jun. 24, 1991),1.
Rifure Co., "English Abstract (Abridged)", JP App. No. 70141/1991, (Jul. 12, 1991),1.
Sakomoto, Susumu "English Abstract", JP patent No. 1181871, (Jul. 19, 1989),1.
Yamamori, Seiji "English Abstract", JP Patent App. No. 5000156 (JP Opened Patent App. No. 00156/1993), (Jan. 8, 1993),1.
Kubo, Tsugio "English Abstract", JP Patent App. No. 317401/1993, (Dec. 3, 1993),1.
Pola Chemical, "English Abstract (abridged)", JP App. No. 72491/1980, (May 20, 1980),1.
Horiuchi, Tetsoshirou "English Abstract", JP patent app. No. 155367/1995, (Jun. 20, 1995),1.
Yokoyama, Mitsuhiro "English Abstract", JP Patent App. No. 182783/1997, (Jul. 15, 1997),1.
Nakamura, Shigemi "English Abstract", JP App. No. 276387/1997, (Oct. 28, 1997),1.
Nakayama, Toru "English Abstract", JP App. No. 047253/1999, (Feb. 23, 1999),1.
Maget, Henri "English Abstract", JP App. No. 91380/1983, (Sep. 6, 1983),1.
Nishimura, Haruo "English Abstract", JP App. No. 305870/1988, (Dec. 13, 1988),1.

(56) References Cited

OTHER PUBLICATIONS

Hatta, O. "English Abstract (abridged)", JP App. No. 00374/1940, (Jan. 16, 1940),1.
Bushey, Scott "International Search Report", PCT US 99/11775 (corresponding to U.S. Appl. No. 09/028,372), (Aug. 20, 1999),1-2.
Bushey, Scott "Written Opinion of the International Searching Authority", PCT US 99/11775 (corresponding to U.S. Appl. No. 09/028,372), (Jun. 11, 2001),1-4.
Kim, Christopher "Non Final Office Action", U.S. Appl. No. 09/649,563, (Jan. 21, 2003),1-5.
Zheng, Li "Notification of the First Office Action", Chinese Application 200580008690.4 (corresponding to U.S. Appl. No. 10/708,253), (Jul. 3, 2009),1-6.
Unknown Japanese Patent Examiner, "Japanese Office Action (and English translation Summary)", JP App. No. 2006/554202 (Corresponding to U.S. Appl. No. 10/708,253), (Nov. 24, 2010),1-6.
Paik, Sang Y., "International Search Report", PCT US 05/05031 (Corresponding to U.S. Appl. No. 10/708,253), (Oct. 14, 2005),1-4.
Paik, Sang Y., "Written Opinion of the International Searching Authority", PCT US 05/05031 (Corresponding to U.S. Appl. No. 10/708,253), (Oct. 14, 2005),1-4.
Paik, Sang Y., "Non Final Office Action", U.S. Appl. No. 10/708,253, (Jul. 1, 2005),1-7.
Paik, Sang Y., "Final Office Action", U.S. Appl. No. 10/708,253, (Apr. 10, 2006),1-6.
Shearer, Daniel "Non Final Office Action", U.S. Appl. No. 13/323,332, (Apr. 23, 2012),1-9.
Wood, Jonathan "Non Final Office Action", U.S. Appl. No. 11/923,490, (Feb. 15, 2011),1-15.
Shearer, Daniel "Final Office Action", U.S. Appl. No. 11/923,490, (Aug. 16, 2011),1-10.
Bae, Yeo W., "International Search Report", PCT/US2011/066895 (corresponding to U.S. Appl. No. 13/335,192., (Jul. 30, 2012),1-3.
Bae, Yeo W., "Written Opinion of the International Searching Authority", PCT/US2011/066895 (corresponding to U.S. Appl. No. 13/335,192)., (Jul. 30, 2012),1-5.
Horikiri, et al., "Patent Abstracts of Japan (English Translation)", Japanese Publication No. 05-262602, (Oct. 12, 1993),1.
Okada, Yoshiro "Bibliographical Data and English Abstract", JP Patent App. No. 62-033102, (Feb. 13, 1987),1-2.
Shearer, Daniel R., "Non-Final Office Action", U.S. Appl. No. 13/323,341, (Jan. 30, 2013),1-10.
Nakamura, Shigemi "English Language Abstract", JP Patent Publication No. 09-276386, (Oct. 28, 1997),1-2.
Nakamura, Shigemi "English Language Abstract", JP Patent Publication No. 09-253185, (Sep. 30, 1997),1-2.
Kim, Seung B., "International Search Report", PCT App. No. PCT/US2012/040743 (Corresponding to U.S. Appl. No. 13/487,976), (Jul. 25, 2013),1-9.
Kim, Seung B., "Written Opinion of the International Searching Authority", PCT App. No. PCT/US2012/040743 (Corresponding to U.S. Appl. No. 13/487,976), (Jul. 25, 2013),1-4.
Shearer, Daniel R., "Final Office Action", U.S. Appl. No. 13/323,341, (Jun. 4, 2013),1-12.
Kim, Christopher S., "Non-Final Office Action", U.S. Appl. No. 12/950,053, (Mar. 12, 2013),1-5.
Kim, Christopher S., "Final Office Action", U.S. Appl. No. 12/950,053, (Jul. 25, 2013),1-9.

\* cited by examiner

DEVICE FOR DELIVERY OF VOLATILE LIQUIDS TO GASEOUS ENVIRONMENT UTILIZING A GAS GENERATING CELL

CROSS-REFERENCE TO RELATED APPLICATIONS

This application claims the benefit of priority of U.S. Provisional Patent Application 61/493,127 entitled, "Orientation Independent Device For Delivery of Volatile Liquids to Gaseous Environment Utilizing an Electrochemical Gas Generating Cell" filed on Jun. 3, 2011. The contents of this application are incorporated by reference herein it their entirety.

BACKGROUND

Fragrance delivery devices are used to emit fragrances into the ambient environment. The use of fragrances can enhance a user's experience within a particular space. For example, fragrances may increase a potential buyer's desire to make a food or retail purchase. In another example, less desirable fragrances may discourage entry or lingering within a particular space.

SUMMARY

Embodiments of a delivery apparatus include a volatile agent source, a controller, and an emanator material. The volatile agent source stores a volume of a volatile agent such as a fragrance. The volatile agent source includes an outlet for delivery of the volatile agent from the volatile agent source. The controller controls a delivery rate of the volatile agent from the volatile agent source. The emanator material is disposed at approximately the outlet of the volatile agent source. The emanator material absorbs at least a portion of the volatile agent and maintains the volatile agent until the volatile agent evaporates into an ambient environment. Other embodiments of the apparatus are also described.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

Embodiments of the present invention have been developed in response to the present state of the art and, in particular, in response to the problems and needs in the art that have not yet been fully solved by currently available structures and methods. Accordingly, embodiments of the invention have been developed to provide structures and methods to overcome various shortcomings of the prior art. The features and advantages of various embodiments of the invention will become more fully apparent from the following description and appended claims, or may be learned by practice of the invention as set forth hereinafter.

While many embodiments are described herein, at least some embodiments relate to a delivery apparatus to deliver a fragrance or other volatile agent to an ambient environment. In one embodiment, the delivery apparatus includes a volatile agent source, a controller, and an emanator material. The volatile agent source stores a volume of a volatile agent such as a fragrance. The volatile agent source includes an outlet for delivery of the volatile agent from the volatile agent source. The controller controls a delivery rate of the volatile agent from the volatile agent source. The emanator material is disposed at approximately the outlet of the volatile agent source.

The emanator material absorbs at least a portion of the volatile agent and maintains the volatile agent until the volatile agent evaporates into an ambient environment. Other embodiments of the delivery apparatus are also described.

Figure 1:
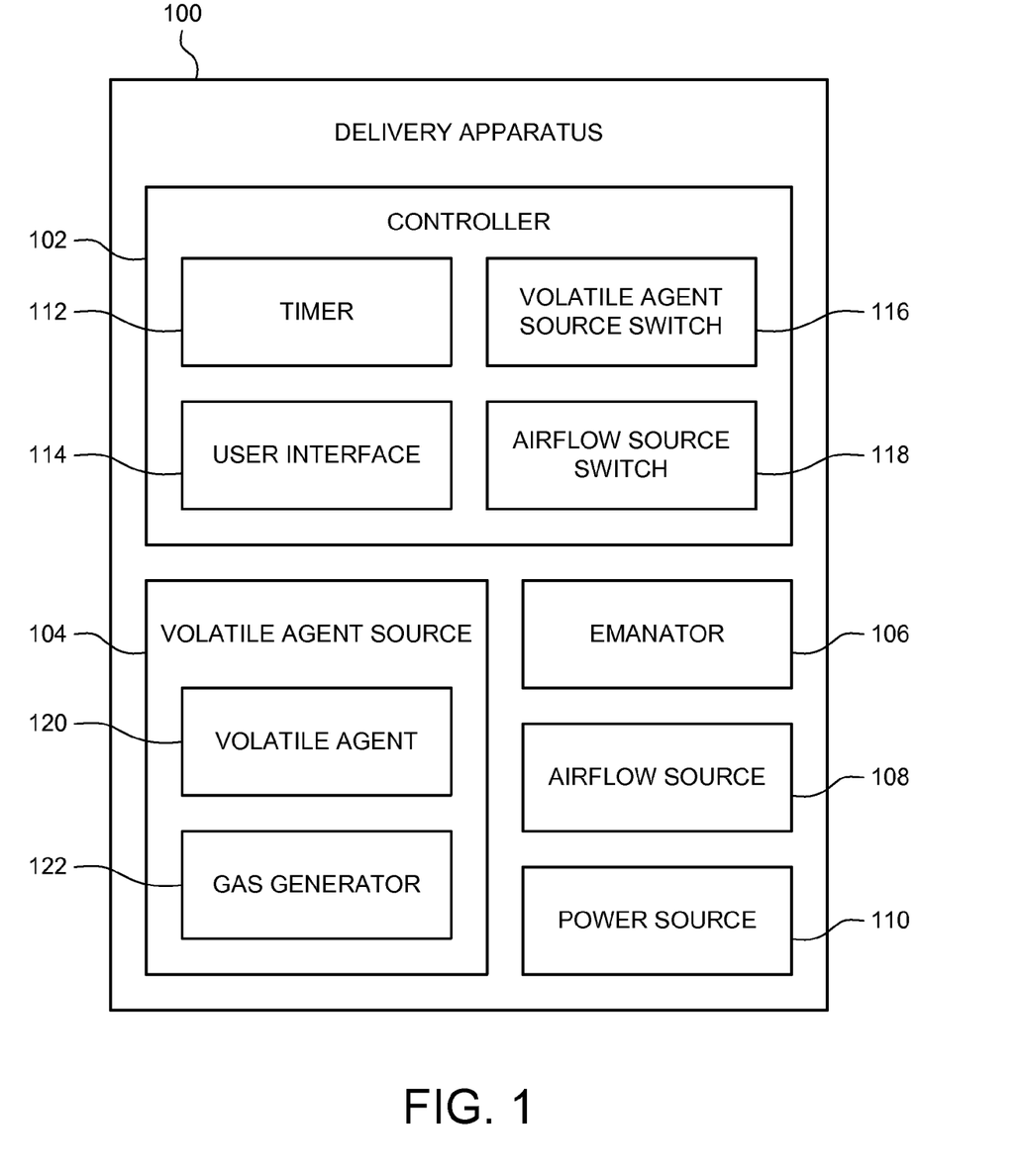
FIG. 1 depicts a schematic diagram of one embodiment of a delivery apparatus.

FIG. 1 depicts a schematic diagram of one embodiment of a delivery apparatus 100. The illustrated delivery apparatus 100 includes a controller 102, a volatile agent source 104, an emanator 106, an airflow source 108, and a power source 110. The illustrated controller 102 includes a timer 112, a user interface 114, a volatile agent source switch 116, and an airflow source switch 118. The illustrated volatile agent source includes a volatile agent 120 and a gas generator 122. Although the delivery apparatus 100 is shown and described with certain components and functionality, other embodiments of the delivery apparatus 100 may include fewer or more components to implement less or more functionality.

In general, the controller 102 of the delivery apparatus 100 controls delivery of the volatile agent 120 from the volatile agent source 104 into an ambient environment. There are various ways in which the controller 102 can control this process. In one embodiment, the controller 102 controls generation of the volatile agent 120 within the volatile agent source 104. In another embodiment, the controller 102 controls generation of another gas or fluid which forces the volatile agent 120 out of the volatile agent source 104. The volatile agent 120 can be allowed to evaporate, transpire, or convect naturally into the ambient environment. Alternatively, the transfer of the volatile agent 120 to the ambient environment can be facilitated by artificial airflow or other forces.

In some embodiments, the controller 102 controls a delivery rate of the volatile agent 120 over a target delivery period. The delivery rate may be consistent or variable. Similarly, the delivery period may be consistent or intermittent. For example, the controller 102 may implement a delivery period that includes intermittent durations of delivery separated by durations of non-delivery. In another example, the controller 102 may implement a delivery period that maintains a consistent delivery rate for given settings over the delivery entire period. In other embodiments, the controller 102 may implement variable delivery rates and periods based on one or more ambient feedback inputs such as temperature, barometric pressure, and so forth. For example, if the ambient temperature went up the controller 102 would decrease the current so that the gas volumetric flow rate of the device would stay the same. Conversely, if the ambient temperature went down the controller 102 would increase the current so that the gas volumetric flow rate of the device would stay the same. Similarly, if an increase in pressure was detected, the controller 102 would increase the current to maintain volumetric flow. Conversely, if a pressure drop was detected, the controller 102 would decrease the current to maintain a constant volumetric flow.

In one embodiment, the controller 102 implements the timer 112 to track periods of delivery and/or non-delivery. In some embodiments, the controller 102 uses the timer 112 to set a specific delivery period. For example, the delivery period may be about 60 days or, in some embodiments, up to about 90 days or more.

In some embodiments, the controller 102 includes the user interface 114 so that a user can input one or more instructions and/or receive one or more feedback signals. The instructions may include, but are not limited to, an instruction to start delivery, an instruction to stop temporarily or permanently delivery, an instruction to increase or decrease a delivery rate, in instruction to implement or change a mix ratio between multiple volatile agents, and so forth. The feedback signals may include audible feedback (e.g., tones or verbal recordings), visual feedback (e.g., indicator lights, readout displays), or other types of feedback that are recognizable by a user.

The controller 102 implements the volatile agent source switch 116 to control delivery of the volatile agent 120 from the volatile agent source 104. The volatile agent source switch 116 may be any type of switch to control absolute or variable delivery rates of the volatile agent 120 from the volatile agent source 104. In some embodiment, the controller 102 controls the volatile agent source switch 116 according to a time indicated by the timer 112.

The controller 102 implements the airflow source switch 118 to control operation of the airflow source 108. In general, the airflow source 108 provides airflow to help deliver the volatile agent 120 from the delivery apparatus 100. The airflow source switch 118 may be any type of switch to control absolute or variable airflow rates of the airflow source 108. Accordingly, the airflow source switch 118 may be adjusted such that the airflow starts and stops at different intervals. Similarly, the airflow source switch 118 may be adjusted such that the airflow intensity can be adjusted. In some embodiment, the controller 102 controls the airflow source switch 118 according to a time indicated by the timer 112.

Additionally, the controller 102 may control the airflow source switch 118 and the volatile agent source switch 116 separately or together. When these switches 116 and 118 are controlled together, the volatile agent source 104 and the airflow source 108 may be controlled synchronously or in an otherwise combined relative manner. For example, the controller 102 may control the volatile agent source switch 116 to turn on the volatile agent source 104 at the same time that the controller 102 controls the airflow source switch 118 to turn on the airflow source 108. Similarly, the controller 102 may control the volatile agent source switch 116 to increase a delivery rate of the volatile agent source 104 at the same time that the controller 102 controls the airflow source switch 118 to increase an airflow intensity of the airflow source 108. In another example, the controller may receive a user input via the user interface 114 to decrease the airflow intensity the delivery apparatus 100, in which case the controller 102 can control the airflow source switch 118 to decrease an airflow intensity of the airflow source 108 at the same time that the controller 102 controls the volatile agent source switch 116 to decrease a delivery rate of the volatile agent 120 from the volatile agent source 104.

The volatile agent source 104 may be any kind of device which generates, stores, and or facilitates delivery of the volatile agent 120 into the ambient environment. The volatile agent 120 may be a fluid or a gas. In some embodiments, the volatile agent 120 is a liquid fragrance. Alternatively, the volatile agent 120 may be another type of substance.

In one embodiment, the amount of volatile agent 120 that is generated, stored, and/or delivered by the volatile agent source 104 is up to about 200 cc by volume. In another embodiment, the amount of volatile agent 120 that is generated, stored, and/or delivered by the volatile agent source 104 is up to about 300 cc by volume. Other embodiments may generate, store, and/or deliver other amounts of the volatile agent 120.

In some embodiments, the volatile agent source 104 includes the gas generator 122 to generate a gas or other volume of substance within the volatile agent source 104. The generation of the gas or other substance may be used to displace the volatile agent 120 and, consequently, deliver the volatile agent 120 from the volatile agent source 104.

As the volatile agent 120 is expelled or delivered from the volatile agent source 104, at least some of the volatile agent 120 is absorbed by the emanator 106. For reference, the emanator 106 is also referred to herein as an emanator material. In one embodiment, the emanator 106 is a storage and delivery vehicle for the volatile agent 120.

The emanator 106 has one or more properties which determine or influence the delivery rate/time of the volatile agent 120 from the delivery apparatus 120. Some examples of such properties include, but are not limited to an evaporation rate, a wicking property, a retention property, and a clogging property. By noting these and other properties of the emanator 106, a proper combination of the emanator 106 and the volatile agent 120 can be selected to determine or influence the performance parameters of the delivery agent 100, as a whole. In other words, the volatile agent 120 can be chosen by taking into consideration some or all of the parameters of the emanator 106. In one embodiment, the delivery apparatus 100 has a design parameter for a specific emanation rate of the volatile agent 120 (e.g., in g/sqcm/hour units). In one embodiment, the maximum pumping rate achievable based on the environmental factors and combinations of controller settings is determined such that the exposed or total area of the emanator 106 exceeds the minimum amount required to emanate the maximum delivery possible for the volatile agent 120.

The airflow source 108 also may determine or influence the delivery rate of the volatile agent 120 from the delivery apparatus 100. In general, the airflow source 108 generates an artificial airflow that is directed at, near, or through the emanator 106. As the generated airflow passed by the emanator 106, the airflow causes forced convection of the volatile agent 120 from the emanator 106 and into the ambient environment.

In one embodiment, the power source 110 provides all of the necessary power for all of the components within the delivery apparatus 100. The power source may include any type of power generator or transfer device. In one embodiment, the power source is a battery which stores electrical energy and emits direct current (DC) at a predetermined voltage. Alternatively, the power source 110 may include a conductor for connection to an external power source such as an external battery (not shown) or an external alternating current (AC) source (not shown). In some embodiments, the controller 102 controls some or all of the power transferred to any of the components within the delivery apparatus 100.

Figure 2:
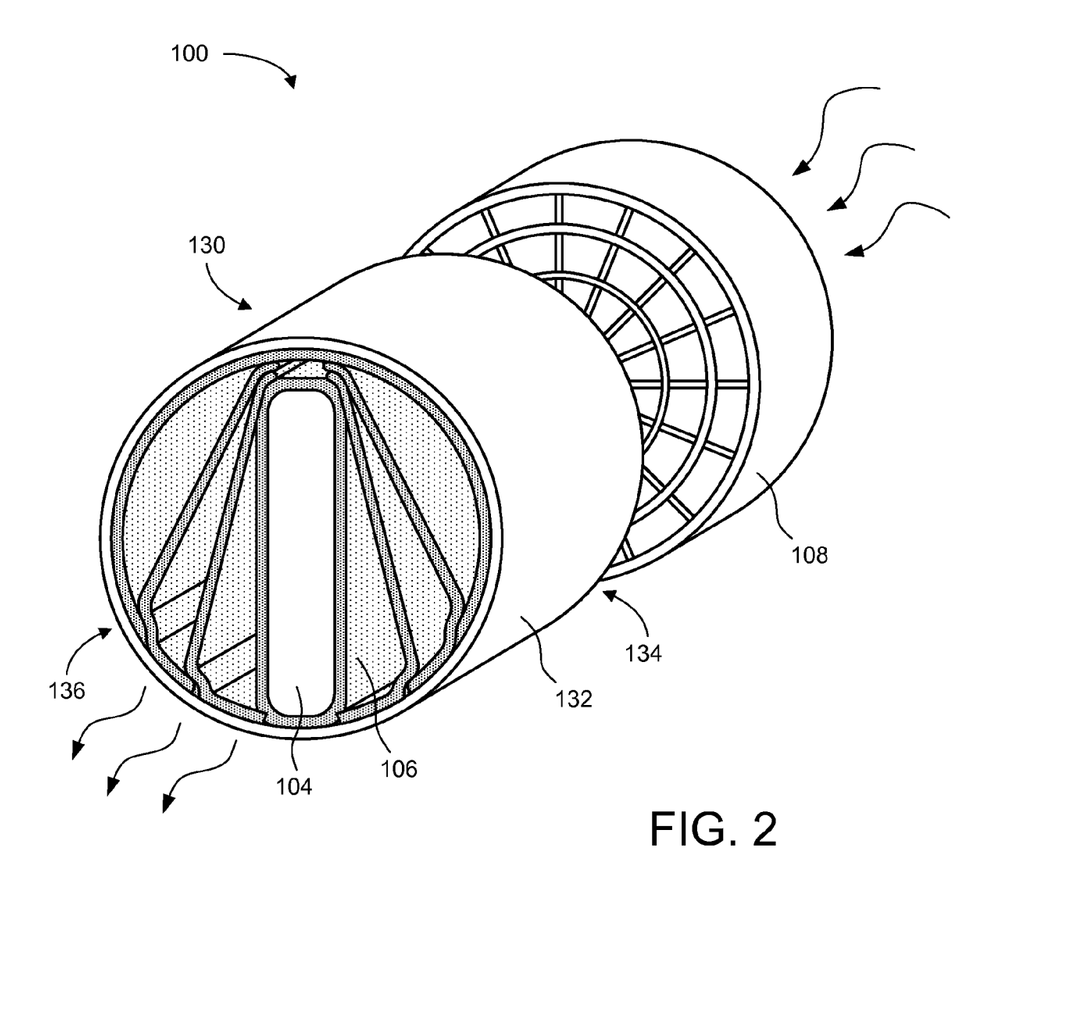
FIG. 2 depicts a diagram of another embodiment of the delivery apparatus of FIG. 1.

FIG. 2 depicts a diagram of another embodiment of the delivery apparatus 100 of FIG. 1. In the illustrated embodiment, the volatile agent source 104 and the emanator 106 are disposed within a cartridge 130.

The use of a cartridge 130 format may be useful, in some embodiments, to facilitate easy replacement of consumable components of the delivery apparatus 100. Also, embodiments of the delivery apparatus 100 may be stand-alone units or may be configured to retrofit into preexisting housings.

In particular, the volatile agent source 104 and the emanator 106 are within an interior space of a housing 132 of the cartridge 130. The depicted housing 132 is cylindrical with a circular cross-section. The housing 132 defines an interior channel with an inlet 134 and an outlet 136. For reference, the inlet 134 is also referred to herein as an input, an input side, or an inlet side of the housing 132. Similarly, the outlet 136 is also referred to herein as an output, an output side, or an outlet side of the housing 132. In some embodiments, the outlet 136 of the housing 132 is also designated as the outlet of the delivery apparatus 100, as a whole. The inlet 134 and the outlet 136 are located on opposite ends of to the cylindrical housing 132. In an embodiment which relies on natural convection of the volatile agent 120 from the delivery apparatus 100, either end of the housing 132 may be designated as the inlet 134 or outlet 136.

In the illustrated embodiment, the volatile agent source 104 and the emanatory 106 are located within the interior space of the cartridge 132. Under control of the controller 102 (refer to FIG. 1), the volatile agent source 104 releases the volatile agent 120 within the cartridge 132. At least a portion of the emanator 106 is wrapped around or adjacent to an outlet (not shown) of the volatile agent source 104 so that the delivered volatile agent 120 is absorbed into the emanator 120. Once absorbed, the volatile agent 120 can be transferred through natural or forced convention from the emanator 106 to the ambient environment.

The emanator 106 includes one or more sheets of materials that have sufficient wicking properties to absorb the volatile agent 120. Some examples of potential emanator materials include, but are not necessarily limited to cellulose fiber, non-woven fibers, woven fibers, naturally occurring fibers, sponge, gauze, and foam. In other embodiments, the emanator 106 may be made from another material or a combination of materials. In some embodiments, the emanator 106 includes material that has a liquid wicking action which is greater than or equal to the force of gravity. This allows the delivery apparatus 106 to be oriented in any direction.

In FIG. 2, the emanator 106 includes a plurality of sheets arranged in a pattern within the cartridge 132. A first sheet of material wraps around an outer surface of the volatile agent source 104. Another sheet of material wraps the inside sidewall of the housing 132 (i.e. the inner sidewall of the channel inside the housing 132). Other sheets of material disposed to extend within the open space between the first two sheets, so that the sheets are individually suspended from about the top of the volatile agent source 120 to lower portions of the inner wall of the housing 132. This arrangement of the sheets of the emanator 106 defines a plurality of discrete airflow paths between the sheets. The discrete airflow paths may be substantially linear or straight between the inlet 134 and the outlet 136 of the housing 132. Alternatively, the discrete airflow paths may be non-linear, indirect, or circuitous between the inlet 134 and the outlet 136. A significant surface area of each sheet is exposed to open air space(s) within the housing 132 to allow the volatile agent 120 absorbed within the emanator 106 to convect or transfer to the ambient environment and travel out of the housing 132 and the delivery apparatus 100. Although a certain number and configuration of sheets are described and shown in FIG. 2, other embodiments may use a different number of sheets and/or a different configuration within the housing 132. However, each configuration may allow ample exposure to the ambient environment and allow wicking to occur from one sheet to another. In one embodiment, the sheets of emanator material 106 are oriented with the smallest dimensions toward the inlet 134 and the outlet 136.

In the illustrated embodiment, the airflow source 108 is located at or adjacent to the inlet 134 of the housing 132. The airflow source 108 provides a source or airflow into the inlet 134 of the housing 132. In one embodiment, the airflow source 108 is a fan, and the controller 102 controls the electrical power (e.g., voltage and current) supplied to the fan, which controls the revolutions per minute (RPM) of the fan and, hence, the airflow intensity. In other embodiments, the airflow source 108 may be another type of gas generator or storage device. For example, the airflow source 108 may be a $CO_2$ cartridge, and the controller 102 may control a release rate of the $CO_2$ from the cartridge.

This airflow through the housing 132 provides forced convection to promote increased delivery of the volatile agent 120 into the ambient environment. Although the airflow source 108 is shown as a separate component that is not within the housing 132 of the cartridge 130, in other embodiments the cartridge 130 may include different combinations of replaceable components, including the airflow source 108, the controller 102, the power source 110, and so forth.

Figure 3A:
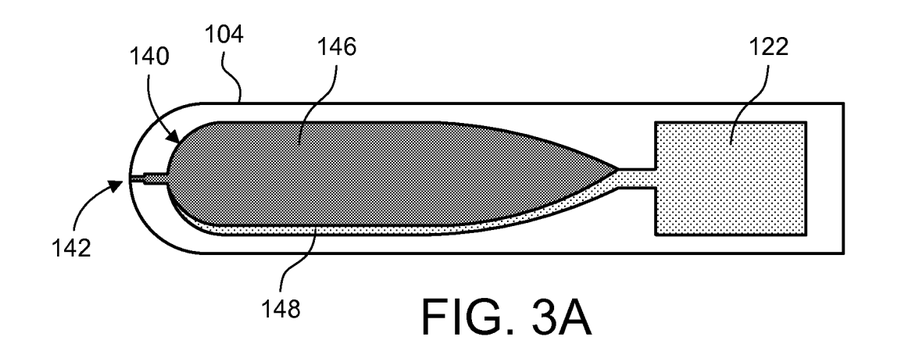
FIG. 3A depicts a diagram of one embodiment of the volatile agent source of FIG. 1 in a pre-delivery state.
Figure 3B:
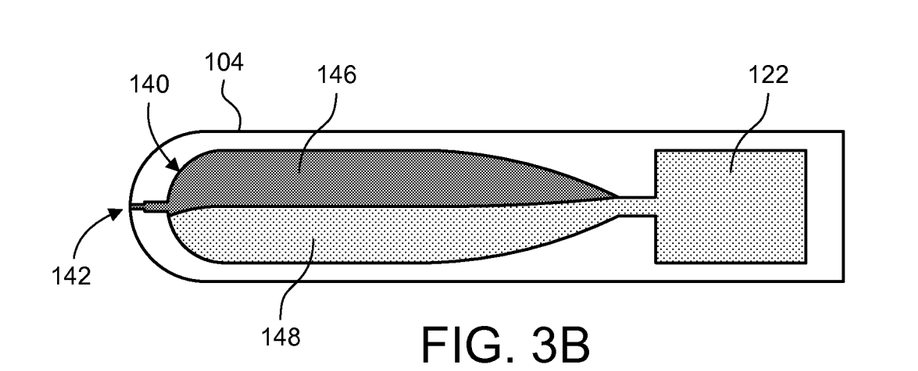
FIG. 3B depicts a diagram of the volatile agent source of FIG. 3A in an active delivery state.
Figure 3C:
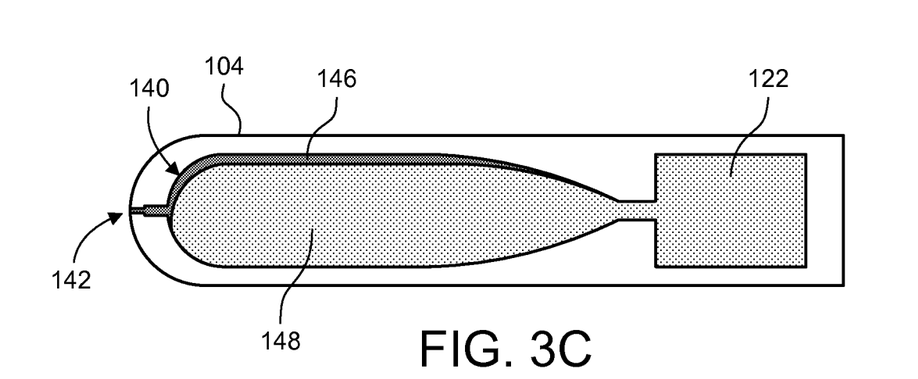
FIG. 3C depicts a diagram of the volatile agent source of FIG. 3A in a post-delivery state.
Figure 4:
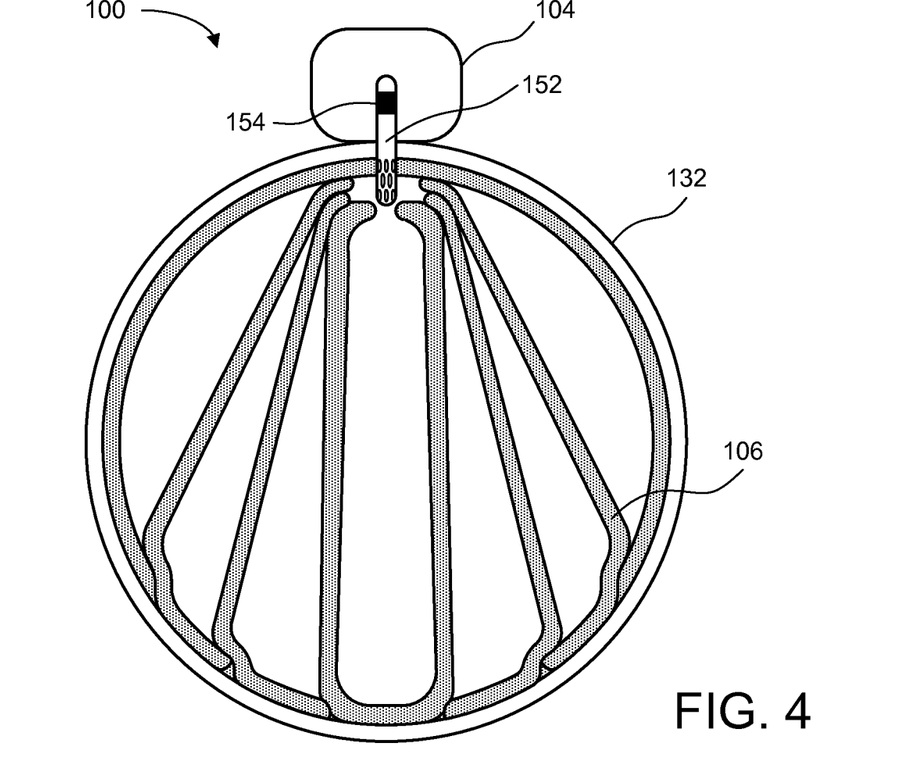
FIG. 4 depicts a diagram of another embodiment of the delivery apparatus of FIG. 2.
Figure 5:
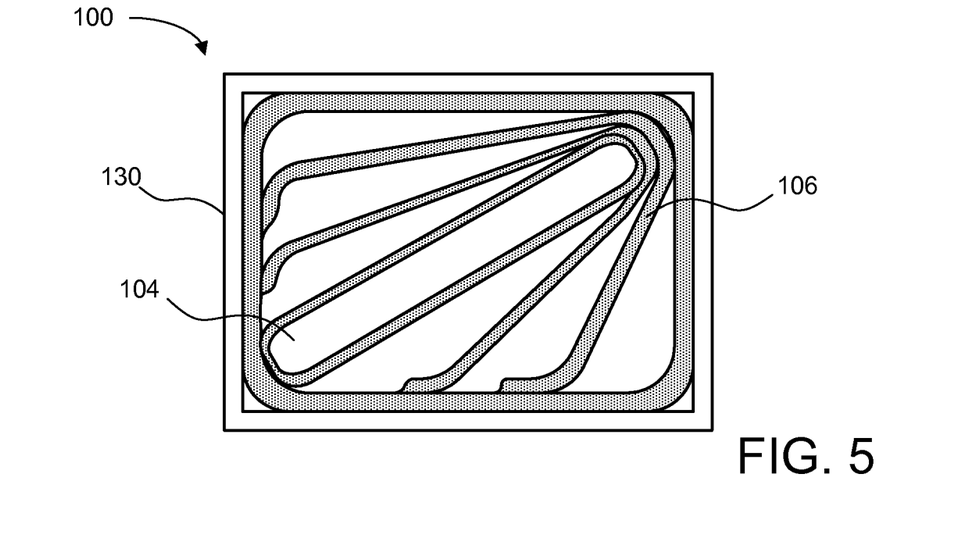
FIG. 5 depicts a diagram of another embodiment of the delivery apparatus of FIG. 2 with a rectangular housing and emanator material arrangement.

FIG. 3A depicts a diagram of one embodiment of the volatile agent source 104 of FIG. 1 in a pre-delivery state. Although a particular type of volatile agent source 104 is shown in FIGS. 3A-3C and described below, other embodiments of the delivery agent 100 may include different types of volatile agent sources 104.

The illustrated volatile agent source 104 electrochemically generates oxygen within a constrained enclosure 140. The oxygen may be generated by the to gas generator 122. The gas generator 122 may include a gas generating cell, or "gas cell", containing copper hydroxide. The gas cell may include a resistor sized to result in a target current passing through the gas cell in response to the DC voltage. The resistor can be sized such that the nominal delivery period will be a set time period. When the DC voltage is applied to the gas cell, copper plates at the cathode while oxygen evolves at the anode. When the circuit is switched off, the electrochemical processes and the evolution of oxygen stop. In one embodiment, the gas cell delivers a specified amount of oxygen which correspondingly will deliver a substantially similar amount of the volatile agent 120 through an outlet 142 to the emanator 106.

In one embodiment, the constrained enclosure 140 implements a constrained double bag (CDB) arrangement. The CDB arrangement may provide orientation independence of the volatile agent source 104 and the delivery apparatus 100. The CDB arrangement includes a liquid bag 146 and a gas bag 148 within the constrained enclosure 140. The liquid bag 146 is impermeable to fluid transfer, except at the outlet 142, and contains the volatile agent 120. The gas bag 148 is impermeable to gas transfer, except at the inlet from the gas generator 122. Although the illustrated CDB arrangement is described as implementing a liquid bag 146 and a gas bag 148, in other embodiments, the CDB arrangement may include other types of volatile agent chambers and/or gas chambers that are formed without the use of bags.

In a specific embodiment, the liquid bag 146 and the gas bag 148 have an excess volume to allow for variations from the nominal conditions and still meet the critical delivery parameters. The liquid bag 146 may be constructed of material known to tolerate the chemical properties of the volatile agent 120. In one embodiment, the liquid bag 146 is constructed of Barex® made by INEOS. The gas bag 148 may be constructed of material known to have acceptable barrier properties with respect to the generated gas. Due to the constrained enclosure surrounding both the liquid bag 146 and the gas bag 148, as the gas bag 148 fills, the liquid bag 148 empties in a 1:1 relationship.

The fluid flow rate of the volatile agent 120 may be divided by the approximate cross sectional area to determine estimated flow velocity ranges. The evaporation of the volatile agent 120 may be estimated or determined at the to minimum and nominal temperatures at the minimum and nominal flow.

In the pre-delivery state shown in FIG. 3A, the gas bag 148 is empty or nearly empty and the liquid bag is full with the volatile agent 120. The volume of the two bags together is restricted by the overall volume of the constrained enclosure 140.

FIG. 3B depicts a diagram of the volatile agent source 104 of FIG. 3A in an active delivery state. In the active delivery state, the controller 102 controls the volatile agent source switch 116 to apply a voltage to the gas generator 122. In response, gas is generated and begins to fill the gas bag 148. As gas fills the gas bag 148, the volatile agent 120 within the liquid bag 146 is forced out through the outlet 142 due to the restricted overall volume of the constrained enclosure 140. In this way, the volatile agent 120 is forced out of the reservoir at substantially the same rate as the gas bag 148 is filled. In some embodiments, the dimensions of the liquid bag 146 are approximately the same as the dimensions of the gas bag 148.

In alternative embodiments, the gas generator 122 may include copper, hydroxide, alkali, carbon, carbonate, and/or mixtures thereof. In yet another embodiment, the gas generator 122 generates hydrogen gas. In another embodiment, the gas generator 122 includes a zinc anode and water.

FIG. 3C depicts a diagram of the volatile agent source 104 of FIG. 3A in a post-delivery state. In the illustrated state, the gas bag 148 is essentially full, and substantially all of the volatile agent 120 from the liquid bag 146 has been expelled from the volatile agent source 104.

The gas generated to fill the gas bag 148 is subject to known the gas laws:

$$V=nRT/P, \text{ where}$$

V=gas volume
n=number of moles gas
R=gas constant=82.057 cc atm/mol K
T=temperature in degrees Kelvin
P=pressure in atmospheres In one embodiment, the moles of gas generated by the gas generator to 122 are about 2.6 e-6 per Amp-S. Thus, the higher the electrical current and longer time, the more gas will be contained in the gas bag 148.

Also, pressure varies with elevation approximately according to the relationship:

$$P(\text{atmospheres})=[1-(2.25577e-5\times H]5.25588$$

where H is the elevation in meters.

Thus, the gas volume for a given quantity of gas generated is greater at higher elevations. This pressure effect results in higher rates delivered at higher elevations. Thus, the amount of volatile agent 120 delivered can be greater. In order to control the amount of volatile agent 120 that is delivered at various elevations, it may be useful to standardize certain delivery parameters so that different, but acceptable amounts of volatile agent are delivered at each elevation level. In some embodiments, this standardized delivery approach may take into account the distribution of population as a function of elevation. Table 1 below shows a global population distribution versus elevation.

TABLE 1

Global population distribution at different elevation ranges.

| Cum | Elevation | | Pressure | | Diff. between Sea level rate and high elev. Back pressure (psig) | | | |
|---|---|---|---|---|---|---|---|---|
| Pop | range (m) | | range (atm) | | 0 | 15 | 30 | 45 |
| 82% | 0 | 700 | 1.00 | 0.92 | 8.4% | 4.1% | 2.7% | 2.0% |
| 12% | 700 | 1500 | 0.92 | 0.83 | 17.3% | 8.4% | 5.5% | 4.1% |
| 4.5% | 1500 | 2000 | 0.83 | 0.78 | 22.5% | 10.9% | 7.2% | 5.4% |
| 1.5% | 2000 | 3100 | 0.78 | 0.68 | 33.0% | 16.0% | 10.6% | 7.9% |

From the data of Table 1, approximately 82% of the population lives below 700 meters (2300 feet), 12% lives between 700-1,500 meters (2,300-4,921 feet), 4.5% lives between 1,500-2,000 meters (4,821-6,562 feet), and the remaining 1.5% live between about 2,000-3,100 meters (6,562-10,171 feet). This means that about 94% of the global population lives below 1500 meters.

Table 1 also shows the barometric pressure ranges corresponding to the various elevation ranges.

If the delivery device 100 discharges with negligible back pressure, then there will be approximately 8.4% difference in rate between users at sea level and users at 700 meters elevation (covering about 82% of the population). If that range is expanded to 1,500 meters (encompassing about 94% of the population), to then the difference is about 17.3%. Extending the range further to 2,000 meters (encompassing about 98.5% or the population), then the difference over the range is 22.5%. To encompass the virtually all the world population, up to 3,100 meters, the difference is 33.1%.

From a practical view, the 6% of the population living at elevations over 1,500 meters are accustomed to being required to make some adjustments from appliances, equipment, and cooking recipes due to the lower air pressure.

The effect of elevation can be reduced by operating the delivery device 100 with backpressure. For example, if a check valve (see FIG. 4) is utilized on the fluid outlet of the volatile agent source 104, then the barometric pressure effect from elevation is diminished. This is because the volume of the gas generated by the gas generator 122 is affected by the total pressure which is the back pressure plus the barometric pressure. Table 1 shows the effect of back pressure and elevation range on the difference in delivery rate. Thus, without back pressure the difference in rate between sea level and 1,500 meters is 17.3%, while that difference drops to about 8.4%, 5.5%, and 4.1% with back pressures of 15, 30 and 45 psig.

According to the gas law, the volume of the gas varies according to the absolute temperature. For example, if the nominal rate is based on operation at 22° C. (71.6° F., 295 K), the rate will be higher if the temperature is higher and lower of the temperature is lower. Raising the absolute temperature by 5% will result in 5% faster rate, increasing to 36.75° C. (98.1° F., 309.75 K). Decreasing absolute temperature by 5% will result in 5% lower rate, decreasing to 7.25° C. (45.0° F., 280.25 K). The temperature effect can be reduced somewhat by using a thermister (not shown) in the electrical circuit in combination with one or more resistors. For example, a thermister with rising resistance with temperature will reduce the rate at which oxygen is produced by the anode of the gas generator 122 if the temperature rises, offsetting the rise in gas volume occurring from the temperature rise, thus offsetting the effects.

In some embodiments, the gas generator 122 may take input voltage from an existing unit to be retrofitted or supplied within. In one embodiment, the gas generator 122 utilizes the same circuit as the airflow source 108. The pump rate to deliver the volatile agent 120 over a target duration under a set of nominal conditions is affected by variations in the input voltage. In one example, the actual voltage at the gas generator 122 is less than 0.5 V, so if the nominal line voltage is 12 V, then about 11.5 V will be brought down by use of a resistor (or resistor/thermistor combination). If the actual voltage is higher or lower than the nominal level, then the rate will be affected almost linearly—higher if the voltage is higher, and lower if the voltage is lower.

Some features of the embodiments may include selective delivery modes such as the duration and the rate of volatile agent delivery and operational parameters such as those listed in Table 2 below.

TABLE 2

| Sample operational parameters<br>Pump parameters | |
|---|---|
| Total pump volume | 200 cc |
| Critical delivery mode | Nominal, min, or max |
| Critical delivery parameter | Duration (days), rate (cc/h) |
| Nominal, Min, Max temp | ° C. (72° C.) |
| Nominal elevation, Min, Max | Meter (350, 700, 1500) |
| Nominal hours per day | 11 |
| Nominal duty cycle | 50% |
| Nominal days per week | 7 |
| Nominal back pressure | 0 |
| Nominal line voltage, min, max | 12 V |
| Activation bolus | Cc |
| Activation method | TBD |
| Volatile fluid viscosity | 1 cp +/− 20% |
| Other requirements? | Drop Vibration Storage |
| Dimensional | Existing refill shell, fan, electrical connector |

In one embodiment, a back pressure of 15 psi will approximately double the amount of copper hydroxide needed. Similarly, a back pressure of 30 psi will triple the amount. The area of the anode may be affected somewhat by the maximum rate contemplated by any of the operation mode scenarios.

Each of these performance parameters may be used to estimate the minimum area required or desired for the emanator 106 so that the volatile agent 120 can transfer from the liquid phase in the emanator 106 to the gas phase in the ambient air.

FIG. 4 depicts a diagram of another embodiment of the delivery apparatus 100 of FIG. 2. In the depicted embodiment, the volatile agent source 104 is located outside of the housing 132. As the volatile agent 120 is expelled to from the volatile agent source 104, a conduit 152 directs the volatile agent 120 to one or more sheets of the emanator 106 within the housing 132. The conduit may have a single outlet or multiple outlets. Additionally, a check valve 152 is located at or within the conduit 152 in order to provide back pressure at the outlet of the volatile agent source 104. In this way, the check valve 154 prevents flow from the volatile agent source 104 until the gas generator 122 within the volatile agent source 104 creates sufficient pressure to exceed the back pressure of the check valve 154.

Also, by locating the volatile agent source 104 outside of the housing 132, the volatile agent source 104 does not block airflow within this housing 132. Consequently, in some embodiments transfer of the volatile agent 120 to the ambient environment may be increased due to the additional exposed area of the emanator 106.

FIG. 5 depicts a diagram of another embodiment of the delivery apparatus 100 of FIG. 2 with a rectangular housing 132 and emanator material 106 arrangement.

In other embodiments, the housing 132 may have a different shape. For example, the housing 132 may have a conical shape so that the subassembly including the emanator 106 may have a cross section or two cross sections which are of smaller dimension than a third cross section, where the one of the smaller cross sections is oriented toward the inlet 134 and/or the outlet 136.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A delivery apparatus comprising:
a volatile agent source configured to store a volume of a volatile agent, wherein the volatile agent source comprises an outlet for delivery of the volatile agent from the volatile agent source;
a controller coupled to the volatile agent source, wherein the controller is configured to control a delivery rate of the volatile agent from the volatile agent source;
an emanator material disposed at approximately the outlet of the volatile agent source, wherein the emanator material is configured to absorb at least a portion of the volatile agent and to maintain the volatile agent until the volatile agent evaporates into an ambient environment; and
a channel, wherein the emanator material is arranged within the channel to define a plurality of discrete airflow paths that are divided by corresponding portions of the emanator material.

2. The delivery apparatus of claim 1, further comprising an airflow source coupled to the controller, wherein the airflow source is configured to direct airflow by the emanator material to evaporate the volatile agent from the emanator material into the ambient environment.

3. The delivery apparatus of claim 2, wherein the airflow source comprises a fan disposed on an inlet side of the emanator material.

4. The delivery apparatus of claim 2, wherein the controller is further configured to control the airflow directed by the emanator material.

5. The delivery apparatus of claim 4, wherein the controller is further configured to control the airflow source in conjunction controlling delivery of the volatile agent from the volatile agent source.

6. The delivery apparatus of claim 1, wherein the volatile agent source comprises a volatile agent chamber, wherein the volatile agent chamber holds the volatile agent until the volatile agent is forced out of the volatile agent chamber.

7. The delivery apparatus of claim 6, wherein the volatile agent chamber comprises a fluid impermeable bag, and the volatile agent is disposed within the fluid impermeable bag.

8. The delivery apparatus of claim 6, wherein the volatile agent source further comprises:
a gas chamber disposed adjacent to the volatile agent chamber, wherein the gas chamber and the volatile agent chamber are disposed within a constrained enclosure; and
a gas generator coupled to the gas chamber, wherein the gas generator is configured to generate gas on demand within the gas chamber;
wherein the volatile agent within the volatile agent chamber experiences an increase in pressure within the constrained enclosure due to generation of the gas within the gas chamber and corresponding expansion of the gas chamber within the constrained enclosure.

9. The delivery apparatus of claim 8, wherein the gas generator comprises a gas cell, wherein the gas cell requires an applied voltage from a power source to generate the gas.

10. The delivery apparatus of claim 9, wherein the gas cell is further configured to generate oxygen gas.

11. The delivery apparatus of claim 9, wherein the gas cell comprises a mixture of copper hydroxide, an alkali hydroxide, and carbon.

12. The delivery apparatus of claim 9, wherein the gas cell is further configured to generate hydrogen gas.

13. The delivery apparatus of claim 9, wherein the gas cell comprises a zinc anode and water.

14. The delivery apparatus of claim 8, wherein the volatile agent chamber and the gas chamber within the constrained enclosure are disposed in a constrained double bag (CDB) arrangement.

15. The delivery apparatus of claim 8, wherein the gas chamber comprises a gas impermeable bag, and the gas generator is disposed within the gas impermeable bag.

16. The delivery apparatus of claim 8, wherein the volatile agent chamber further comprises a check valve coupled to the outlet of the volatile agent source, wherein the check valve is configured to open to deliver the volatile agent from the volatile agent chamber in response to the pressure of the volatile agent reaching a threshold within the volatile agent chamber.

17. The delivery apparatus of claim 8, wherein the volatile agent chamber further comprises a conduit coupled between an outlet of the volatile agent chamber and the outlet of the volatile agent source, wherein the conduit is configured to direct the volatile agent from the volatile agent chamber to the emanator material.

18. The delivery apparatus of claim 8, wherein the controller is further configured to control the generation of the gas within the gas chamber.

19. The delivery apparatus of claim 1, wherein the volatile agent source comprises a volatile agent generator, wherein the volatile agent generator is configured to produce the volatile agent on demand.

20. The delivery apparatus of claim 1, further comprising an airflow source disposed within the channel approximately adjacent to the emanator material, wherein the airflow source directs airflow through a plurality of discrete airflow paths defined by the emanator material to evaporate the volatile agent from the emanator material into the ambient environment.

21. The delivery apparatus of claim 1, wherein the emanator material is disposed on substantially all of an inner sidewall of the channel.

22. The delivery apparatus of claim 1, wherein the volatile agent source is disposed within the channel, and the emanator material is disposed to substantially cover at least a portion of an outer surface of the volatile agent source.

23. The delivery apparatus of claim 1, wherein the volatile agent source is disposed outside of the channel, and the volatile agent source further comprises a conduit which intrudes into an inner volume of the channel to direct the volatile agent to the emanator material within the channel.

24. The delivery apparatus of claim 1, wherein the emanator material has a wicking property to absorb the volatile agent.

25. The delivery apparatus of claim 24, wherein the wicking property of the emanator material is at least equal to a force of gravity on the volatile agent absorbed within the emanator material.

26. The delivery apparatus of claim 24, wherein the emanator material comprises a sheet of a wicking material from a class of wicking materials, wherein the class of wicking materials comprises cellulose fiber, non-woven fibers, woven fibers, naturally occurring fibers, sponge, gauze, and foam.

27. The delivery apparatus of claim 24, wherein the emanator material comprises an arrangement of a plurality of sheets of a wicking material, wherein the sheets are arranged to define a plurality of discrete airflow paths that are divided by corresponding sheets of the wicking material.

28. A delivery apparatus comprising:
- a volatile agent source configured to store a volume of a volatile agent, wherein the volatile agent source comprises an outlet for delivery of the volatile agent from the volatile agent source, wherein the volatile agent source comprises a volatile agent chamber, wherein the volatile agent chamber holds the volatile agent until the volatile agent is forced out of the volatile agent chamber;
- a controller coupled to the volatile agent source, wherein the controller is configured to control a delivery rate of the volatile agent from the volatile agent source;
- an emanator material disposed at approximately the outlet of the volatile agent source, wherein the emanator material is configured to absorb at least a portion of the volatile agent and to maintain the volatile agent until the volatile agent evaporates into an ambient environment; and
- wherein the volatile agent source further comprises:
  - a gas chamber disposed adjacent to the volatile agent chamber, wherein the gas chamber and the volatile agent chamber are disposed within a constrained enclosure; and
  - a gas generator coupled to the gas chamber, wherein the gas generator is configured to generate gas on demand within the gas chamber; and
  - wherein the volatile agent within the volatile agent chamber experiences an increase in pressure within the constrained enclosure due to generation of the gas within the gas chamber and corresponding expansion of the gas chamber within the constrained enclosure.

29. A delivery apparatus comprising:
- a volatile agent source configured to store a volume of a volatile agent, wherein the volatile agent source comprises an outlet for delivery of the volatile agent from the volatile agent source;
- a controller coupled to the volatile agent source, wherein the controller is configured to control a delivery rate of the volatile agent from the volatile agent source;
- an emanator material disposed at approximately the outlet of the volatile agent source, wherein the emanator material is configured to absorb at least a portion of the volatile agent and to maintain the volatile agent until the volatile agent evaporates into an ambient environment wherein the emanator material has a wicking property to absorb the volatile agent; and
- wherein the emanator material comprises an arrangement of a plurality of sheets of a wicking material, wherein the sheets are arranged to define a plurality of discrete airflow paths that are divided by corresponding sheets of the wicking material.

* * * * *